United States Patent [19]

Raabe et al.

[11] Patent Number: 4,532,239
[45] Date of Patent: Jul. 30, 1985

[54] N-PHENOXYPROPANOL-N'-PYRIDAZINYL ETHYLENDIAMINES AS β-RECEPTOR BLOCKERS

[75] Inventors: Thomas Raabe, Rodenbach; Helmut Bohn, Schöneck; Piero A. Martorana, Bad Homburg; Rolf-Eberhard Nitz, Frankfurt am Main, all of Fed. Rep. of Germany

[73] Assignee: Cassella Aktiengesellschaft, Fed. Rep. of Germany

[21] Appl. No.: 563,538

[22] Filed: Dec. 20, 1983

Related U.S. Application Data

[63] Continuation of Ser. No. 332,238, Dec. 18, 1981, abandoned.

[30] Foreign Application Priority Data

Dec. 22, 1980 [DE] Fed. Rep. of Germany ....... 3048487

[51] Int. Cl.³ .................... C07D 237/22; A61K 31/50
[52] U.S. Cl. .................................. 514/247; 544/114; 544/238; 544/239; 544/241
[58] Field of Search .............. 544/238, 239, 241, 114; 424/250

[56] References Cited

U.S. PATENT DOCUMENTS

| | | | |
|---|---|---|---|
| 3,723,524 | 3/1973 | Augstein et al. | 424/250 |
| 3,931,177 | 1/1976 | Coates et al. | 424/250 |
| 4,027,027 | 5/1977 | Jaeggi et al. | 424/266 |
| 4,088,764 | 5/1978 | Raabe et al. | 424/251 |
| 4,115,575 | 9/1978 | Frei et al. | 424/250 |
| 4,216,314 | 8/1980 | Raabe et al. | 544/123 |
| 4,255,425 | 3/1981 | White | 544/241 |

OTHER PUBLICATIONS

Wolff, Manfred, Burger's Medicinal Chemistry, 4th, vol. III, John Wiley, New York (1981), pp. 270–273.

Primary Examiner—Donald G. Daus
Assistant Examiner—G. Hendricks
Attorney, Agent, or Firm—Berman, Aisenberg & Platt

[57] ABSTRACT

Basically-substituted pyridazines of the formula:

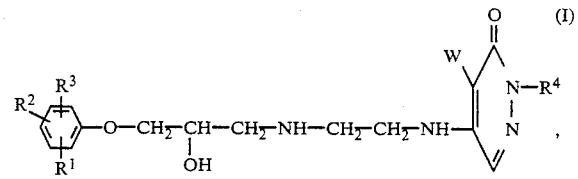

wherein $R^1$, $R^2$ and $R^3$, independently of one another, denote hydrogen, halogen, hydroxyl, nitro, trifluoromethyl, alkyl, alkoxyalkyl, alkenyl, alkynyl, cycloalkyl, cycloalkenyl, phenyl, alkoxy, hydroxyalkoxy, alkoxyalkoxy, alkenyloxy, alkynyloxy, cycloalkoxy, phenalkoxy, alkanoyl, alkanoylamino and —NH—CO—$R^9$, $R^9$ representing morpholino, piperidino or 1-pyrrolididinyl, or an optionally substituted ureido radical, $R^4$ denotes hydrogen or lower alkyl and W denotes hydrogen, chlorine or bromine; and the acid-addition salts thereof are useful alone or in pharmaceutical preparations for treating cardiac complaints, circulatory complaints and high blood pressure. Several methods for preparing the basically-substituted pyridazines are also provided.

20 Claims, No Drawings

N-PHENOXYPROPANOL-N'-PYRIDAZINYL ETHYLENDIAMINES AS β-RECEPTOR BLOCKERS

This is a continuation of Ser. No. 06/332,238, filed Dec. 18, 1981, now abandoned.

The present invention relates to pharmacologically valuable basically substituted pyridazines of the formula

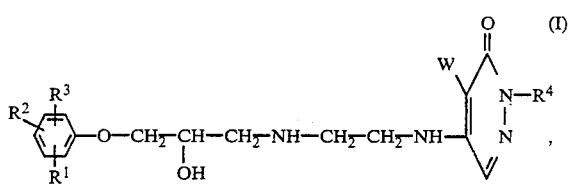

wherein $R^1$, $R^2$ and $R^3$, independently of one another, denote hydrogen, halogen, hydroxyl, nitro, trifluoromethyl, alkyl, alkoxyalkyl, alkenyl, alkynyl, cycloalkyl, cycloalkenyl, phenyl, alkoxy, hydroxyalkoxy, alkoxyalkoxy, alkenyloxy, alkynyloxy, cycloalkoxy, phenakoxy, alkanoyl, alkanoylamino and —NH—CO—$R^9$, $R^9$ representing morpholino, piperidino or 1-pyrrolididinyl, or an optionally substituted ureido radical, $R^4$ denotes hydrogen or lower alkyl and W denotes hydrogen, chlorine or bromine; and to the acid-addition salts thereof. These substituted pyridazines include physiologically-active and pharmacologically-acceptable compounds wherein $R^1$, $R^2$ and $R^3$ are independently selected from the group consisting of hydrogen; fluorine; chlorine; bromine; hydroxyl; nitro; trifluoromethyl; alkyl having from 1 to 8 C atoms; alkoxyalkyl having from 2 to 6 C atoms; alkenyl having up to 6 C atoms; alkynyl having up to 6 C atoms; cycloalkyl having a ring size of from 5 to 8 C atoms; phenyl; alkoxy having from 1 to 8 C atoms; hydroxyalkoxy having from 2 to 6 C atoms; alkoxyalkoxy having a total of up to 8 C atoms; alkenyloxy having up to 6 C atoms; alkynyloxy having up to 6 C atoms; cycloalkoxy having a ring size of from 5 to 8 C atoms; benzyloxy; phenethoxy; alkanoyl having from 1 to 6 C atoms; acylamino having up to 11 C atoms in the acyl radical; an —NH—CO—$R^9$ radical, $R^9$ being a member selected from the group consisting of morpholino, piperidino or 1-pyrrolidinyl; ureido; ureido which is monosubstituted in the 3-position by cycloalkyl having 5 or 6 C atoms; ureido which is monosubstituted or disubstituted in the 3-position by alkyl having 1 to 6 C atoms and/or alkenyl having 3 to 6 C atoms.

The compounds of formula I have an asymetric C atom in the alkanolamine side chain and therefore exist in racemic and optically active forms. Within the scope of the present invention, the compounds of formula I include possible stereoisomers optically active compounds and mixtures thereof, particularly racemates.

The substituents mentioned for $R^1$, $R^2$ and $R^3$ have the following meanings, in particular, in addition to hydrogen, halogen, hydroxyl, nitro, trifluoromethyl and phenyl: alkyl having 1 to 8, preferably 1 to 4 C atoms, for example methyl, ethyl, propyl, isopropyl, n-butyl, isobutyl, tert.-butyl, sec.-butyl, n-pentyl, isopentyl, neopentyl, tert.-pentyl, n-hexyl, isohexyl, n-heptyl and n-octyl; alkenyl having up to 6, preferably 3 or 4 C atoms, for example vinyl, allyl, 1-propenyl, isopropenyl, methallyl, crotyl, 2-pentenyl and 2-hexenyl; alkynyl having up to 6, preferably 3 or 4 C atoms, for example propagyl; cycloalkyl having a ring size of from 5 to 8, preferably 5 or 6, C atoms, for example cyclopentyl and cyclohexyl; cycloalkenyl having a ring size of from 5 to 8, preferably 5 or 6 C atoms, for example cyclopentenyl; alkoxy having 1 to 8 C atoms, for example methoxy, ethoxy, propoxy, butoxy, isopropoxy, isohexyloxy, n-heptyloxy, n-octyloxy and pentoxy; cycloalkoxy having a ring size of from 5 to 8 C atoms in the cycloalkyl part, preferably cyclopentoxy and cyclohexyloxy; alkenyloxy having up to 6, preferably 3 or 4, C atoms, for example allyloxy, methallyloxy, crotyloxy and 2-hexenyloxy; alkinyloxy having up to 6, preferably 3 or 4, C atoms, for example propargyloxy; alkanoyl having 1 to 6 C atoms, for example formyl, acetyl, propionyl, butyryl, isobutyryl, valeryl, isovaleryl and pivaloyl; alkoxyalkoxy having a total of up to 8 C atoms, the alkoxyalkoxy radical being of the form $R^6O$—$R^5O$—, and $R^5$ representing an alkylene radical having 2 to 7 C atoms, $R^6$ representing an alkyl radical having 1 to 6 C atoms, and it also being possible for the radicals $R^5$ and/or $R^6$ to be branched in the case of 3 and more C atoms. Examples of suitable alkoxyalkoxy radicals are: 2-methoxy-ethoxy, 2-ethoxy-ethoxy, 3-methoxy-n-propoxy, 2-methoxy-n-propoxy, 4-methoxy-n-butoxy, 3-ethoxy-n-propoxy, 2-ethoxy-n-propoxy, 4-ethoxy-n-butoxy, 3-ethoxy-n-butoxy, 2-ethoxy-n-butoxy, 2,2-dimethyl-2-ethoxy-ethoxy, 3-(n-propoxy)-n-propoxy, 2-(n-propoxy)-n-propoxy, 3-(iso-propoxy)-n-propoxy, 2-(iso-propoxy)-n-propoxy, 2-(n-propoxy)-ethoxy, 2-(iso-propoxy)-ethoxy, 4-(n-propoxy)-n-butoxy, 3-(n-propoxy)-n-butoxy, 2-(n-butoxy)-ethoxy, 2-(sec.-butoxy)-ethoxy, 2-(tert.-butoxy)-ethoxy, 3-(n-butoxy-n-propoxy, 2-(n-butoxy)-n-propoxy, 3-(iso-butoxy)-n-propoxy, 3-(sec.-butoxy)-n-propoxy, 3-(tert.-butoxy)-n-propoxy, 4-(n-butoxy)-n-butoxy, 3-(n-butoxy)-n-butoxy, 2-(n-butoxy)-n-butoxy, 4-(iso-butoxy)-n-butoxy, 3-(isobutoxy)-n-butoxy, 2-(sec.-butoxy)-n-butoxy, 2,2-dimethyl-2-(n-butoxy)-ethoxy, 2-(n-butoxy)-1-methyl-ethoxy, 2-(iso-butoxy)-2-methyl-ethoxy, 5-methoxy-n-pentoxy, 4-methoxy-n-pentoxy, 3-methoxy-n-pentoxy, 5-ethoxy-n-pentoxy, 4-ethoxy-n-pentoxy, 3-ethoxy-n-pentoxy, 5-(n-propoxy)-n-pentoxy, 5-(iso-propoxy)-n-pentoxy, 6-methoxy-n-hexyloxy, 5-methoxy-n-hexyloxy, 4-methoxy-n-hexyloxy, 6-ethoxy-n-hexyloxy, 3-ethoxy-n-hexyloxy and 7-methoxy-n-heptyloxy; alkoxyalkyl having 2 to 6 C atoms, the alkoxyalkyl radical being of the form $R^8O$—$R^7$— and $R^8$ representing an alkyl radical and $R^7$ an alkylene radical, and it being also possible for the radicals $R^8$ and/or $R^7$ to be branched if they contain more than 3 C atoms, for example: methoxy-methyl, ethoxy-methyl, n-propoxy-methyl, iso-propoxy-methyl, n-butoxy-methyl, n-pentoxy-methyl, 2-methoxy-ethyl, 2-ethoxy-ethyl, 2-n-propoxy-ethyl, 2-iso-propoxy-ethyl, 2-n-butoxy-ethyl, 3-methoxy-n-propyl, 3-ethoxy-n-propyl, 3-n-propoxy-n-propyl, 2-methyloxy-2-methyl-ethyl, 2-ethoxy-1-methyl-ethyl, 2-n-propoxy-2-methyl-ethyl, 2-iso-propoxy-1-methyl-ethyl, 4-methoxy-n-butyl, 4-ethoxy-n-butyl and 5-methoxy-n-pentyl; hydroxyalkoxy having 2 to 6 C atoms, for example 2-hydroxy-ethoxy, 3-hydroxy-n-propoxy, 4-hydroxy-n-butoxy, 3-hydroxy-n-butoxy, 5-hydroxy-n-pentoxy, 4-hydroxy-n-hexyloxy, 2-hydroxy-n-hexyloxy and 2-hydroxy-n-propoxy; phenalkoxy, for example phenethoxy, and particularly benzyloxy; ureido or a ureido radical which is substituted in the 3-position by alkyl having 1 to 6 C atoms, preferably 1 to 4 C atoms, alkenyl having 3 to 6 C atoms, or cycloalkyl having 5 or 6 C atoms, or disubstituted where substitution is by alkyl and/or alkenyl.

Examples of suitable ureido radicals are ureido, 3-methylureido, 3-ethylureido, 3-propylureido, 3-isopropylureido, 3-allylureido, 3-cyclopentylureido, 3-cyclohexylureido, 3,3-dimethylureido and 3,3-diethylureido; fluorine, chlorine or bromine are examples of suitable halogens; and an —NH—CO—R$^9$— radical, R$^9$ representing morpholino, piperidino or 1-pyrrolidinyl.

In the case of the acylamino radical representing R$^1$ and/or R$^2$ and/or R$^3$, the term acyl is understood as meaning the aryl-substituted, aralkyl-substituted or alkyl-substituted carbonyl radical which has up to 11 C atoms and which is derived from an aromatic, aromatic-aliphatic or aliphatic carboxylic acid. Suitable acylamino radicals are, for example, acetamino, propionylamino, butyrylamino, benzoylamino, α- and β-naphthoyl-amino and phenylacetylamino; acetamino and benzoylamino are preferred.

In addition to representing hydrogen, the substituent R$^4$ can represent, in particular, an alkyl radical having 1 to 4 C atoms, for example methyl, ethyl, n-propyl, isopropyl, n-butyl and isobutyl.

Normally, preferred compounds of formula I, or the acid addition salts thereof, are those in which R$^4$ represents hydrogen, or only one of the substituents R$^1$, R$^2$ or R$^3$ is not hydrogen or R$^1$, R$^2$ or R$^3$ is a hydroxyl, an alkoxyalkoxy, an alkoxy, an alkoxyalkyl or a hydroxyalkoxy radical or halogen. Those compounds which have two or more of the abovementioned preferred characteristics, that is to say in which R$^4$ denotes hydrogen and one of the substituents R$^1$, R$^2$ or R$^3$ denotes a hydroxyl, an alkoxyalkoxy, an alkoxy, an alkoxyalkyl or a hydroxyalkoxy radical or halogen and the other two are hydrogen, are particularly preferred. Those radicals which contain no asymmetry centres are normally preferred for R$^1$, R$^2$ and R$^3$.

Inorganic and organic acids are suitable for the formation of acid addition salts with the compounds of formula I. Suitable acids are, for example, hydrochloric acid, hydrobromic acid, naphthalene-1,5-disulphonic acid, phosphoric acid, nitric acid, sulphuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulphamic acid, phenylpropionic acid, gluconic acid, ascorbic acid, isonicotinic acid, methanesulphonic acid, p-toluenesulphonic acid, citric acid or adipic acid. Pharmaceutically-acceptable acid-additon salts are preferred. Those which are not pharmaceutically acceptable are conventionally converted to those which are or to the corresponding free base. The acid addition-salts are obtained in a customary manner by combining the components, advantageously in a suitable diluent or dispersing agent.

For the preparation of the compounds of formula I, a compound of formula V

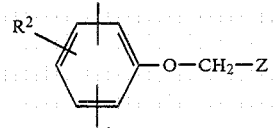

wherein Z represents

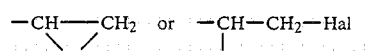

and Hal denotes a halogen atom, particularly chlorine or bromine, is reacted with a compound of formula IV

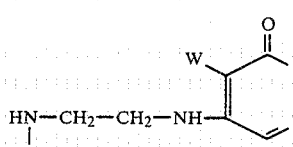

wherein Y represents hydrogen or a radical which can be split off hydrogenolytically, and an available radical which can be split off hydrogenolytically is then split off, by means of hydrogenolysis, from the compound obtained, and the resulting compound is reacted with an acid to give an acid addition salt, if appropriate.

Many radicals which can be split off hydrogenolytically have been known for a long time and proved particularly useful in the area of peptide synthesis. Very instructive papers and reviews were published, particularly by R. A. Boissonnas and G. Preitner, Helvetica Chimica Acta, Volume 36, page 875 (1953) and R. A. Boissonnas, Advances in Organic Chemistry, Volume 3, page 159 et seq. (1973), with many references to the primary literature.

Examples of radicals which can be split of hydrogenolytically are, in particular, benzyl, carbobenzoxy or carbophenoxy which are substituted in the phenyl nucleus by methyl, methoxy, chlorine or phenylazo, as well as carboallyloxy.

Instead of an individual compound of formula V, a mixture of a compound of formula II with a compound, which has the same substituents in the phenyl nucleus, of formula III

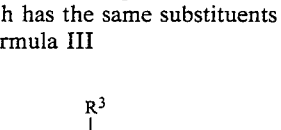

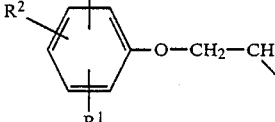

wherein, in formula III, Hal denotes a halogen atom, particularly chlorine or bromine, is alternatively employed.

The reaction of compounds of formula IV and V is normally carried out in a suitable solvent or dispersing agent, in which the reactants are dissolved or suspended. Such solvents or dispersing agents are, for example, water, aromatic hydrocarbons, such as benzene, toluene and xylene; ketones, such as acetone and methyl ethyl ketone; halogenated hydrocarbons, such as chloroform, carbon tetrachloride, chlorobenzene and methylene chloride; ethers, such as tetrahydrofuran and dioxane; sulphoxides, such as dimethylsulphoxide; and tertiary acid amides, such as dimethylformamide and N-methylpyrrolidone. Polar solvents, such as alcohols, are particularly used as the solvents. Suitable alcohols are, for example, methanol, ethanol, isopropanol, tert.-butanol, etc. Alcohols having 1 to 4 C atoms are preferred. The reaction is carried out at temperatures of from 20° C. up to the reflux temperature of the solvent or dispersing agent used. The reaction frequently proceeds at temperatures of from 60° to 100° C. It can be advantageous to employ the starting compound of formula IV in up to 10-fold, or if appropriate even greater, molar excess and/or to add the reaction component of formulae II and III in dissolved or suspended form to the dissolved or suspended reaction component of formula IV. The molar ratio between the compounds of formula II or III and IV can therefore be 1:1 to 1:10 and, if appropriate, even more. In the presence of a compound of formula III, the reaction can also be carried out in the presence of acid-binding agents, such as potassium carbonate, sodium carbonate, triethylamine, etc. Without acid-binding agents, the hydrohalides are customarily obtained, in the case in which Y=hydrogen, the hydrohalides of compounds of formula I.

The reaction of epoxides and halohydrins with compounds containing amino groups and the appropriate reaction conditions are known by themselves. A summary thereof is contained in Houben-Weyl, 4th edition (1965), vol. XI/1, pp. 24–74 and 314–326.

In the reaction of the compounds of formulae IV and V, in the case in which, in formula IV Y represents a radical which can be split off hydrogenolytically, for example a benzyl or carbobenzoxy radical, compounds of formula Ia

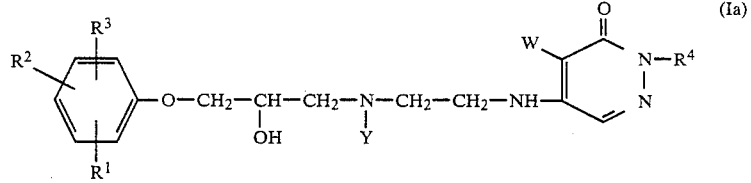

wherein Y represents a radical which can be split off hydrogenolytically, are first obtained. The hydrohalides of the compounds of formula Ia are obtained when compounds of formula III are used, and in the absence of acid-binding aents. The conversion of the compounds of formula Ia, or the hydrohalides thereof, into the compounds of formula I is effected by splitting off the radical Y hydrogenolytically, according to customary processes. In these processes, a compound of formula Ia, or a hydrohalide thereof, is dissolved or suspended in a suitable solvent, such as an alcohol, an ether or a hydrocarbon, such as ethanol, dioxane, toluene, xylene, etc., and is treated with hydrogen, in the presence of a suitable catalyst, such as palladium/charcoal, at temperatures from room temperature (20° C.) up to the reflux temperature of the solvent used. After the catalyst has been filtered off under suction, the compound of formula I can be isolated. In most cases, the radical Y is already split off hydrogenolytically at room temperature (20° C.).

The preparation of the starting compounds of formula IV is effected, e.g., by the reaction of a compound of formula VI

wherein W has the meaning given above and T denotes chlorine or bromine with a compound of formula VII $$H_2N-CH_2-CH_2-NH-X \qquad (VII)$$

wherein X denotes a radical, which can be split off hydrolytically, of a protective group, or the radical Y (=hydrogen or a radical which can be split off hydrogenolytically). An example of a radical which can be split off hydrolytically is the acetyl radical or another acyl radical, that is to say a radical derived from an aliphatic, aromatic or araliphatic carboxylic acid by splitting off OH. As already mentioned, an example of a radical which can be split off hydrogenolytically is the benzyl radical or the carbobenzoxy radical. The reaction of the compounds of formula VI with compounds of formula VII is normally carried out in a suitable solvent or dispersing agent in which the reactants are dissolved or suspended, such as benzene, toluene, xylene, chloroform, methylene chloride, carbon tetrachloride, diethyl ether, dioxane, tetrahydrofuran, dimethylsulphoxide, acetone, methyl ethyl ketone, dimethylformamide, N-methylpyrrolidone, etc. The molar ratio between the compounds of formulae VI and VII is from 1:1 to 1:10 and, if appropriate, even more. The reaction proceeds at room temperature, but is accelerated or carried through to the end by using heat, for example by heating the mixture to a temperature of from 80° to 110° C.

If, in the reaction of a compound of formula VI with a compound of formula VII, X represents hydrogen, the compound of formula VII is advantageously employed in excess, in some cases even as the solvent. If, in the reaction of a compound of formula VI with a compound of formula VII, X represents a protective group which can be split off hydrolytically or hydrogenolytically, and if both reaction components are employed in equimolar quantities, the reaction is advantageously carried out in the presence of an acid-binding agent, such as potassium, carbonate, sodium carbonate, triethylamine, etc.

If, in the reaction of a compound of the general formula VI with a compound of formula VII, X represents a protective group, a compound of formula VIII

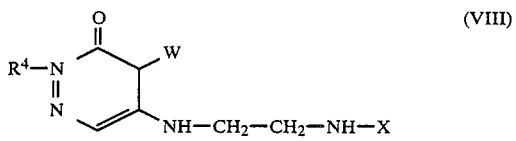

is then first formed, from which compound a compound of formula IV, in which Y represents H, is obtained by splitting off the protective group X by conventional methods, for example by hydrolysis if X represents an acyl radical, or by hydrogenolysis if X represents a radical which can be split off hydrogenolytically.

For the preparation of compounds of formula I, pyridazines of formula VI

wherein $R^4$, W and T have the meanings given above, are alternatively reacted with a diamine of formula IX

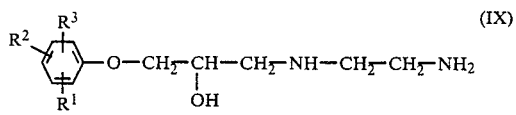

and the compound obtained is optionally reacted with an acid to give an acid-addition salt, if appropriate.

The reaction of a compound of formula VI with a compound of formula IX is normally carried out in a suitable solvent or dispersing agent in which the reactants are dissolved or suspended, such as benzene, toluene, xylene, chloroform, methylene chloride, carbon tetrachloride, chlorobenzene, dioxane, ether, tetrahydrofuran, water, dimethylsulphoxide, dimethylformamide, N-methylpyrrolidone, etc.

The reaction proceeds at room temperature, or it is accelerated or carried through to the end using heat, for example by heating the mixture to a temperature between 80° and 120° C. The molar ratio between compounds of formulae VI and IX is from 1:1 to 1:10 and, if appropriate, even more. If equimolar quantities of the compounds of formulae VI and IX are employed, it is advisable to carry out the reaction in the presence of at least equimolar quantities of an acid-binding agent such as potassium carbonate, sodium carbonate, triethylamine, etc. Without acid-binding agents, the hydrohalides of the compounds of formula I are customarily obtained. The reaction of halogenpyridazines with compounds containing amino groups and the appropriate reaction conditions are also known by themselves. A survey and numerous literature references are given in R. Elderfield, Heterocyclic Compounds (1957), vol. 6, p. 130. German Patent No. 579,391 [CA 27, 4631 (1933)] and Meier, Ringier Druey, Helv.Chim.Acta, vol. 37, pp.510 and 523 (1954) are further examples of references concerning this reaction.

For the preparation of the starting diamines of formula IX, a compound of formula II or III, or a mixture of a compound of formula II with a compound, which has the same substituents on the phenyl nucleus, of formula III, is reacted with a compound of formula VII (X denoting hydrogen or a protective group which can be split off hydrolytically, such as an acetyl radical or another acyl radical). This reaction is normally carried out in a suitable solvent or dispersing agent in which the reactants are dissolved or suspended. Such solvents or dispersing agents are, for example, water; aromatic hydrocarbons, such as benzene, toluene and xylene; ketones, such as acetone and methyl ethyl ketone; halogenated hydrocarbons, such as chloroform, carbon tetrachloride, chlorobenzene and methylene chloride; ethers, such as tetrahydrofuran and dioxane; sulphoxides, such as dimethylsulphoxide; and tertiary acid amides, such as dimethylformamide and N-methylpyrrolidone. Polar solvents, such as alcohols, are particularly used as the solvents. Methanol, ethanol, isopropanol, tert.-butanol, etc. are examples of suitable alcohols.

The reaction is carried out at temperatures of from 20° C. up to the reflux temperature of the solvent or dispersing agent used. The reaction frequently proceeds at temperatures of from 60° to 100° . It can be advantageous to employ the starting compounds of formula VII in up to 10-fold, or if appropriate even greater, molar excess and/or to add the reaction component of formulae II and III in dissolved or suspended form to the dissolved or suspended reaction component of formula VII. The molar ratio between the compounds of formula II or II and VII can be from 1:1 to 1:10 and, if appropriate, even more. In the presence of a compound of formula III, the reaction can also be carried out in the presence of acid-binding agents, such as potassium carbonate, sodium carbonate, etc. Without acid-binding agents, the hydrohalides of the compounds of formula IX are customarily obtained.

If, in the reaction of compounds of formula II or III with a compound of formula VII, X represents a protective group, a compound of formula X

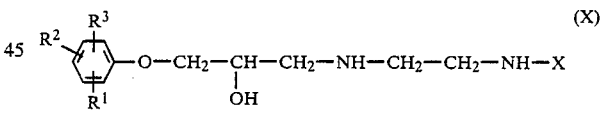

is then first formed, from which compound a compound of formula IX is obtained by splitting off the protective group X according to customary methods, for example by hydrolysis if X represents an acyl radical.

The above methods of preparation are preferred for compounds of the invention in which W denotes chlorine or bromine.

Compounds of the formula I of the present invention in which W is hydrogen can generally be obtained by the methods of preparation described above. Frequently, however, starting compounds of formula IV or VI, in which W denotes hydrogen, are accessible by complicated multi-step synthesis only (see for example Elderfield, Heterocyclic Compounds, vol. 6, p. 130 (1957)). It is thus advantageous to prepare compounds of formula I of the invention, in which W denotes hydrogen, from compounds of formula I of the invention, in which W denotes chlorine or bromine, by exchanging the halogen atom representing W for hydrogen. The selective exchange of the halogen atom which represents W and is linked to the pyridazinone nucleus is effected in a simple manner in a smooth hydrogenation reaction. This is effected, as a rule, by treating with hydrogen a solution or dispersion of the substance in a solvent or dispersant in the presence of a hydrogenating catalyst, for example Raney nickel or a finely divided platinum metal on a suitable carrier, such as palladium on carbon. Lower alkanols having 1–4 C atoms, water or water/alkanol mixtures have been found to be particularly appropriate solvents or dispersants. In order to capture the halide generated during hydrogenation the reaction is carried out in the presence of a base, such as a tertiary amine, MgO, alkali metal acetate or alkali metal hydroxide. The carrying out of such exchange reactions by hydrogenation has been extensively investigated and described, for instance in Houben-Weyl, 4th edition (1965), vol. V/4, pp. 773 et seq., and vol. IV 1c, pp. 364 et seq.

For the preparation of compounds of formula I of the invention, wherein W denotes hydrogen, it is also possible to use, instead of compounds of formula I of the present invention, wherein W is chlorine or bromine, compounds of the formula

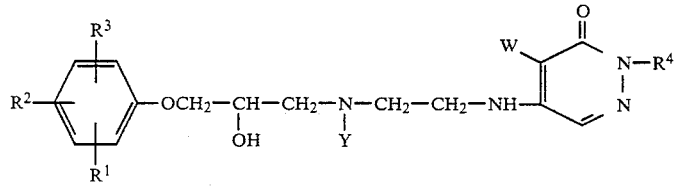

wherein W denotes chlorine or bromine and Y denotes a radical which can be split off hydrogenolytically and wherein $R^1$, $R^2$, $R^3$ and $R^4$ have the meanings indicated above. In the hydrogenation of these compounds in the manner mentioned above and which is in itself known it is possible to exchange in one and the same reaction step both the halogen atom representing W and the radical Y, which can be split off hydrogenolytically, for hydrogen.

Compounds of formula Ia are obtained, as described above, when reacting compounds of formula V with compounds of formula IV wherein Y is a radical capable of being hydrogenolytically split off.

The starting compounds of the general formula VI are either known or can be prepared in a known manner. Starting substances wherein W and T denote chlorine or bromine can be readily prepared by the reaction of hydrazine derivatives of the general formula XI with mucochloric acid, mucobromic acid or the corresponding chlorine-bromine compound (cf. Katritzky, Boulton, Advances in Heterocyclic Chemistry, (1968), vol. 9, pp. 235–236). Mucochloric acid will now be used as an example demonstrating the course of the reaction:

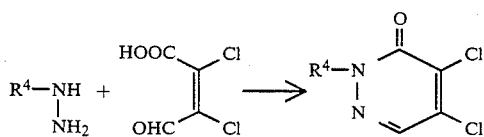

Starting substances of formula VI wherein W denotes hydrogen can, for example, be prepared in accordance with the reaction model shown in R. Elderfield, Heterocyclic Compounds, (1957), vol. 6, p. 130, and proceeding from 4,5-dibromo-pyridazin-3-one.

The compounds of formulae II and III are prepared according to known methods from available starting materials for example by the reaction of an appropriate phenol with epichlorohydrin.

Optically-active forms of the alkylenediamines of formula I are obtained by separation of the corresponding racemic alkylenediamines of formula I by conventional methods, for example by reacting the racemate of a compound of formula I with an optically-active acid, subsequently carrying out, from a suitable diluent or solvent, such as ethanol, a fractional crystallisation of the diastereomeric salt mixture thus obtained, and finally liberating the optically active alkylenediamine from the salt, using a base. Optically active compounds of formula I are also obtained by employing optically active starting compounds III or IX. These optically active starting compounds are obtained from the optically inactive compounds III or IX in a known manner, by resolving the racemic mixture.

The compounds of formula I according to the invention and the acid addition salts thereof have valuable pharmaceutical properties. In particular, they have a very pronounced β-adrenolytic action which is also cardioselective, that is to say the compounds have a higher degree of specificity in the blocking of cardial β-receptors than of peripheral β-receptors, for example β-receptors in the bronchial muscle. In addition, they have strong α-lytic, antiarrhythmic and hypotensive actions. They are therefore suitable, for example, for the treatment or prophylaxis of cardiac complaints and cardiac diseases, such as angina pectoris and cardiac arrhythmias, and also for treating hypertension, without the lungs being affected in the case of sensitive patients.

The compounds of formula I according to the invention are surprisingly significantly superior, in their pharmaceutical action, to the known compounds, of similar structure, of DE-OS (German Published Specification) No. 2,819,629.

The pyridazines according to the invention can therefore be administered to humans, by themselves, in mixtures with one another or in pharmaceutical preparations which contain, as the active constituent, an effective dose of at least one pyridazine according to the invention or one acid addition salt thereof, in addition to customary pharmaceutically acceptable excipients and additives.

Examples of suitable excipients are water, vegetable oils, starch, gelatin, lactose, magnesium stearate, waxes, vaselines, etc. Wetting agents, disintegrating agents, preservatives, etc. can be used, for example, as additives.

The pharmaceutical preparations can be present, for example, in the form of tablets, capsules, aqueous or oleaginous solutions or suspensions, emulsions, injectable aqueous or oleaginous solutions or suspensions, or dispersible powders or aerosol mixtures. In addition to the compounds of formula I, the pharmaceutical preparations can also contain one, or several, other pharmaceutically active substances, for example tranquillizers, such as Luminal, meprobamate and chlorpromazines, and benzodiazepine sedatives, such as diazepam or chlordiazepoxide; vasodilators, such as glycerine trinitrate, pentaerythritol tetranitrate and carbocromen; diuretics, such as chlorothiazide; heart-tonicising agents, such as preparations of digitalis; hypotensive agents, such as Rauwolfia alkaloids and guanethidine; bronochodilators and sympathomimetic agents, such as isoprenaline, osciprenaline, adrenaline and ephedrine; α-adrenergic blocking agents, for example, phentolamine; cardial membrane stabilising agents (antiarrythmics), such as quinidine; and catecholamines, such as noradrenaline.

The examples which follow illustrate in more detail the preparation of the compounds of formula I:

EXAMPLE 1

4.9 g of N-[3-(o-chlorophenoxy)-2-hydroxy-propyl]-ethylenediamine are dissolved in 50 ml of ethanol. A solution of 3.3 g of 4,5-dichloropyridazin-3-one in 50 ml of ethanol is added to the above solution, and the mixture is then heated under reflux for 12 hours. The mixture is then concentrated in vacuo, the residue is digested with a little ethyl acetate and decanted off from the ethyl acetate, and the residue is finally recrystallised from ethanol. The N-[3-(o-chlorophenoxy)-2-hydroxypropyl]-N'-[4-chloro-3-oxopyridaz-5-yl]-ethylenediamine hydrochloride is thus obtained.
Melting point: 219° C.

| Analysis: ($C_{15}H_{19}Cl_3N_4O_3$) | | | | | |
| --- | --- | --- | --- | --- | --- |
| | C | H | Cl | N | O |
| calculated: | 44.0 | 4.6 | 26.0 | 13.7 | 11.7 |
| found: | 44.4 | 4.8 | 27.7 | 13.5 | 12.2 |

Yield: 78% of theory.
The N-[3-(o-chlorophenoxy)-2-hydroxypropyl]-ethylenediamine used as the starting material is prepared as follows:

120 g of ethylenediamine are dissolved in 150 ml of ethanol. A solution of 20 g of o-chlorophenyl glycidyl ether in 40 ml of ethanol is added to the above solution, and the mixture is heated under reflux for 20 hours. Excess ethylenediamine and ethanol are then distilled off in vacuo, and the residue is then distilled in vacuo. The N-[3-(o-chlorophenoxy)-2-hydroxy-propyl]-ethylenediamine is thus obtained as an oil which can be distilled at a boiling point of 190° C./0.4 mm. The 4,5-dichloro-pyridazin-3-one used as the starting material is prepared in a known manner by the reaction of muccochloric acid with hydrazine (for example according to K. Dury, Angew. Chemie 77, page 282 (1965).

EXAMPLE 2

5.1 g of N-[3-(o-ethoxyphenoxy)-2-hydroxy-propyl]-ethylenediamine are dissolved in 50 ml of toluene, and 3 g of potassium carbonate are added to the solution. A solution of 3.6 g of 2-methyl-4,5-dichloro-pyridazin-3-one in 50 ml of toluene is then added to the above solution at room temperature, while stirring, and the mixture is then heated under reflux for 17 hours, while stirring. The mixture is then allowed to cool to room temperature and is filtered off under suction from the inorganic residue, and the filtrate is concentrated in vacuo. The residual oil, which solidifies after a short time, is recrystallised from ethyl acetate. The N-[3-(o-ethoxyphenoxy)-2-hydroxy-propyl]-N'-[2-methyl-3-oxo-4-chloro-pyridaz-5-yl]-ethylenediamine

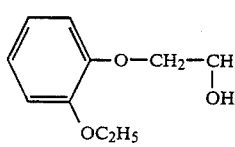 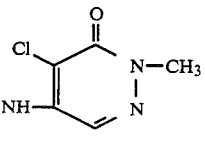

is thus obtained.
Melting point: 120° C.

| Analysis: (C$_{18}$H$_{25}$ClN$_4$O$_4$) | | | | |
|---|---|---|---|---|
| C | H | Cl | N | O |
| calculated: 54.5 | 6.3 | 9.0 | 14.1 | 16.1 |
| found: 54.7 | 6.3 | 9.1 | 13.8 | 16.4 |

Yield: 84% of theory.

The starting materials are prepared analogously to the processes described in Example 1.

EXAMPLE 3

3.8 g of 2',4',6'-trimethyl-phenyl glycidyl ether

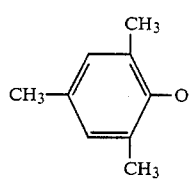

together with 7 g of N-benzyl-N'-[2-butyl-3-oxo-4-chloro-pyridaz-5-yl]-ethylenediamine,

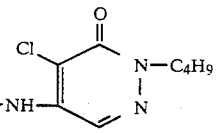

are heated under reflux in 80 ml of ethanol for 1 hour. The mixture is then cooled and the solution is concentrated in vacuo.

The residue is dissolved, without purification, in 120 ml of dioxane, and is then hydrogenated at room temperature with H$_2$, in the presence of Pd/charcoal.

The mixture is then filtered under suction, the filtrate is concentrated in vacuo and the residue is recrystallised from ethanol.

The N-[3-(2',4',6'-trimethylphenoxy)-2-hydroxy-propyl]-N'-[2-butyl-3-oxo-4-chloro-pyridaz-5-yl]-ethylenediamine

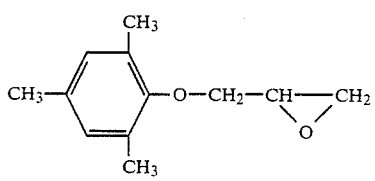

is thus obtained.
Melting point: 137° C.

| Analysis: (C$_{22}$H$_{33}$ClN$_4$O$_3$) | | | | |
|---|---|---|---|---|
| | C | H | Cl | N | O |
| calculated: | 60.5 | 7.6 | 8.1 | 12.8 | 11.0 |
| found: | 60.2 | 7.4 | 8.3 | 12.7 | 11.3 |

Yield: 68% of theory.

The N-benzyl-N'-[2-butyl-3-oxo-4-chloro-pyridaz-5-yl]-ethylenediamine used as the starting material is obtained analogously to Example 2 by the reaction of 2-butyl-4,5-dichloropyridazin-3-one with benzylethylenediamine in boiling toluene, in the presence of 1 mol of potassium carbonate.

EXAMPLE 4

5.85 g of N-[3-(p-pentyloxyphenoxy)-2-hydroxy-propyl]-ethylenediamine of the formula

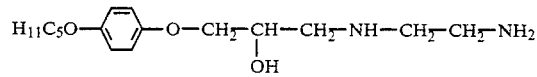

and 5.0 g of 4,5-dibromo-pyridazin-3-one are boiled under reflux in 60 ml of ethanol for 10 hours. The solution obtained is then filtered off and concentrated to give a viscous oil, 100 ml of water and 5–10 ml of ethyl acetate are added to this oily residue with stirring and the pH is adjusted to 9.0 using aqueous 2N-soda solution. This mixture is stirred until the oil has completely crystallised and the solid product obtained is filtered off with suction. The residue (5.4 g corresponding to 58% of theory) is recrystallised from ethanol, 4.2 g of N-[3-(p-pentyloxyphenoxy)-2-hydroxy-propyl]-N'-[3-oxy-4-bromopyridaz-5-yl]-ethylenediamine of the formula

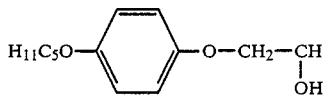 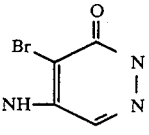

having a melting point of 173°–175° C. are obtained.

| Analysis | C | H | N | O | Br |
|---|---|---|---|---|---|
| calculated C20H29BrN4O4: | 51.14 | 6.2 | 11.9 | 13.6 | 17.0 |
| found: | 51.0 | 6.3 | 11.5 | 13.9 | 16.8 |

EXAMPLE 5

4.13 g of N-(3-phenoxy-2-hydroxy-propyl)-ethylendiamine of the formula

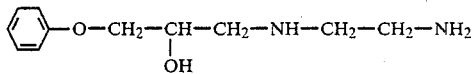

and 5.0 g of 4,5-dibromo-pyrazin-3-one are boiled in 80 ml of anhydrous ethanol under reflux for 30 hours. The solution obtained is filtered off and the filtrate is concentrated. There remains a semi-solid residue, 100 ml of water and 10 ml of ethyl acetate being admixed thereto with stirring. The mixture is now adjusted to a pH of 9.0 by adding aqueous 2N-soda solution, as a result of which the reaction product gradually solidifies.

The solid product is filtered off with suction and the residue is recrystallised from ethanol.

The N-(3-phenoxy-2-hydroxy-propyl)-N'-[3-oxo-4-bromopyridaz-5-yl]ethylenediamine of the formula

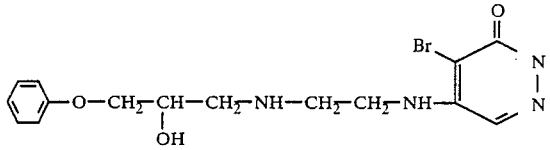

having a melting point of 165° C. is obtained in a yield of 3.9 g corresponding to 52% of theory.

| Analysis: | C | H | N | O | Br |
|---|---|---|---|---|---|
| calculated C15H19BrN4O3: | 47.0 | 5.0 | 14.6 | 12.5 | 20.9 |
| found: | 46.8 | 4.7 | 14.6 | 12.9 | 20.8 |

EXAMPLE 6

3.0 g of N-(3-phenoxy-2-hydroxypropyl)-N'-[4-chloro-3-oxopyridaz-5-yl]-ethylenediamine-hydrochloride of the formula

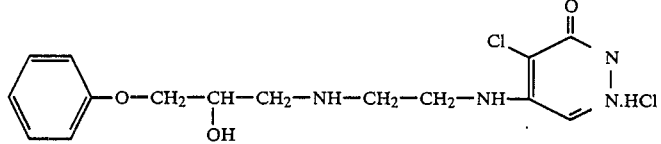

are disolved in 100 ml of 5% by weight caustic soda solution and 0.3 g of 10% strength palladium/carbon are added. Thereafter one hydrates using hydrogen in a shaking apparatus at room temperature and normal pressure until no further hydrogen consumption takes place, whereupon the batch is allowed to stand overnight at room temperature.

The reaction mixture thus obtained is filtered off, the filter residue $R_1$ consisting essentially of the catalyst is stored and the filtrate is evaporated until dry. The residue thus evaporated is kneaded thoroughly with 50 ml of water and the resulting suspension is filtered off with suction. In this way the filter residue $R_2$ is obtained.

The filter residue $R_1$ is agitated thoroughly in 50 ml of ethanol with heating, and the suspension is filtered off the catalyst. The alcoholic residue is evaporated, the residue thus obtained is united with the filter residue $R_2$ and the two are commonly recrystallised from water. 2.0 g (~82% of theory) of N-(3-phenoxy-2-hydroxy-propyl)-N'-[3-oxopyridaz-5-yl]-ethylene-diamine of the formula

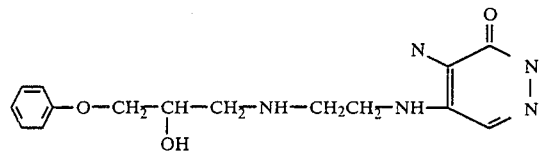

having a melting point of 151°–153° C. are obtained.

| Analysis: | C | H | N | O |
|---|---|---|---|---|
| calculated C15H20N4O3 | 59.18 | 6.63 | 18.41 | 15.78 |
| found: | 59.1 | 6.2 | 18.4 | 16.0 |

EXAMPLE 7

2 g of N-[4-chloro-3-oxopyridaz-5-yl]-ethylenediamine of the formula

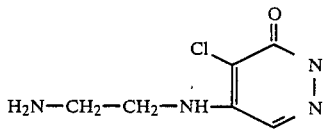

and 1.95 g of o-chlorophenyl-glycide-ether of the formula

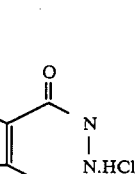

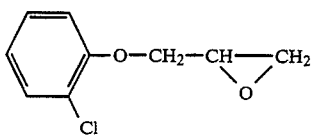

are stirred in 20 ml of anhydrous ethanol, initially at room temperature for 24 hours and subsequently with boiling under reflux for another 40 hours. Then the batch is cooled and the precipitate is filtered off with suction. The filter residue is once more recrystallised from ethanol.

3.1 g (~78.3% of theory) of N-[3-(o-chlorophenoxy)-2-hydroxypropyl]-N'-[4-chloro-3-oxo-pyridaz-5-yl]-ethylenediamine of the formula having a melting point of 170°–172° C. are obtained.

| Analysis | C | H | Cl | N | O |
|---|---|---|---|---|---|
| calculated $C_{15}H_{18}Cl_2N_4O_3$ | 48.24 | 4.86 | 19.02 | 15.01 | 12.86 |
| found: | 48.3 | 4.8 | 19.2 | 15.5 | 12.6 |

The N-[4-chloro-3-oxo-pyridaz-5-yl]-ethylenediamine employed in the above Example was prepared as follows:

11 g of 4,5-dichloro-pyridazin-3-one were added to a solution of 400 g of ethylenediamine in 100 ml of abs.toluene and the mixture was heated in an autoclave to 120° C. for 12 hours.

The solution obtained having cooled, it was evaporated until dry and the residue was recrystallised from ethanol/water. Yield: 9 g (~71.6% of theory).

The compounds mentioned in the following table were prepared in conformity with Examples 1–7:

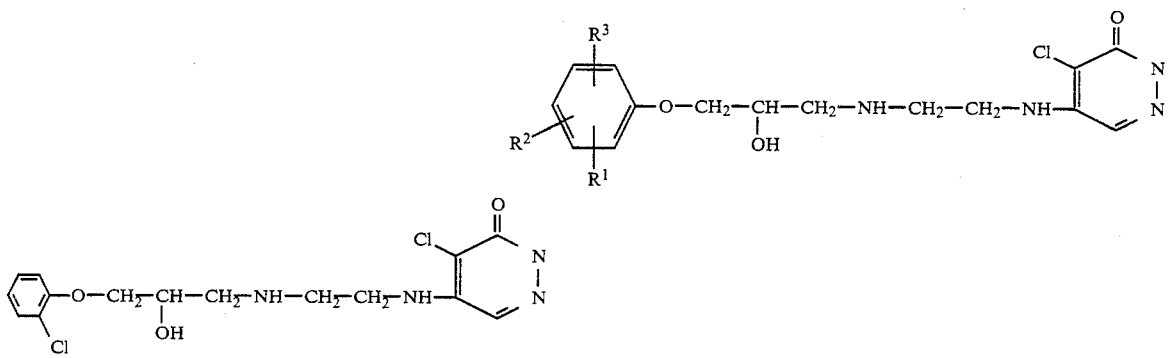

| $R^1$ | $R^2$ | $R^3$ | $R^4$ | Melting point: |
|---|---|---|---|---|
| 4-OC$_4$H$_9$ | H | H | —CH$_3$ | 92° C. |
| 2-OC$_2$H$_5$ | H | H | H | 185° C. Hydrochloride |
| 2-OC$_2$H$_5$ | H | H | —C$_2$H$_5$ | 83° C. |
| 4-OCH$_3$ | H | H | H | 213° C. Hydrochloride |
| 4-OC$_5$H$_{11}$ | H | H | H | 223° C. Hydrochlordie |
| 2-CH$_3$ | H | H | H | 228° C. Hydrochloride |
| H | H | H | H | 198° C. Hydrochloride |
| 4-OC$_4$H$_9$ | H | H | H | 210° C. Hydrochloride |
| 3-OCH$_3$ | H | H | H | 213° C. Hydrochloride |
| 3-OCH$_3$ | 4-OCH$_3$ | 5-OCH$_3$ | —CH$_3$ | 69° C. |
| 2-OCH$_3$ | 3-OCH$_3$ | 4-OCH$_3$ | —C$_3$H$_7$ | 199° C. Hydrochloride |
| 2-![phenyl] | H | H | H | 224° C. Hydrochloride |
| 2-OCH$_2$—CH=CH$_2$ | H | H | —CH$_3$ | 111° C. |
| 2-![cyclopentenyl] | H | H | —C$_2$H$_5$ | 109° C. |
| 2-OCH$_3$ | 6-OCH$_3$ | H | H | 218° C. Hydrochloride |

-continued

| | | | | |
|---|---|---|---|---|
| 4-NH—CO—CH₃ | H | H | —C₃H₇ | 197° C. Hydrochloride |
| 2-O—CH₂—C≡CH | H | H | —CH₃ | 121° C. |
| 4-NH—CO—NH₂ | H | H | H | 113° C. |
| 2-cyclopentyl (H) | H | H | H | 68° C. |
| 4-NH—CO—N(morpholino) | H | H | —C₂H₅ | 219° C. Hydrochloride |
| 4-CH₂—O—CH₃ | H | H | H | 117° C. |
| 4-C(CH₃)₃ | H | H | —C₄H₉ | 71° C. |
| 2-CO—CH₃ | H | H | H | 193° C. Hydrochloride |
| 2-CH₂—OC₂H₅ | H | H | —CH₃ | 211° C. Hydrochloride |
| 4-NH—CO—NH—C₂H₅ | H | H | H | 217° C. Hydrochloride |
| 4-NH—CO—NH—(cyclohexyl) | H | H | H | 119° C. |
| 4-NH—CO—NH—CH₂—CH=CH₂ | H | H | —C₃H₇ | 231° C. Hydrochloride |
| 2-Cl | 6-Cl | H | —C₃H₇ | 101° C. |
| 2-CH₃ | 4-CH₃ | H | —CH₃ | 74° C. |
| 2-CH₃ | 6-CH₃ | H | H | 198° C. Hydrochloride |
| H—OC₂H₉—OC₂H₅ | H | H | —C₂H₅ | 206° C. Hydrochloride |
| 4-OCH₂—CH₂—OH | H | H | —CH₃ | 89° C. |
| 4-C₂H₅ | H | H | —C₂H₅ | 102° C. |
| 2-OCH₃ | 4-CH₂—CH=CH₂ | H | —CH₃ | 107° C. |
| 3-CF₃ | H | H | H | 216° C. Hydrochloride |
| 4-OH | H | H | —C₂H₅ | 122° C. |
| 2-Cl | —Cl | H | H | 199° C. Hydrochloride |
| 4-O—CH₂—(phenyl) | H | H | —C₂H₅ | 204° C. Hydrochloride |
| 4-NO₂ | H | H | H | 57° C. |
| 2-Cl | 5-Cl | H | —CH₃ | 87° C. |
| 4-Br | H | H | —C₂H₅ | 223° C. Hydrochloride |
| 2-cyclohexyl (H) | H | H | H | 196° C. Hydrochloride |
| 2-CH₃ | 4-NO₂ | H | H | 112° C. |
| 3-CH₃ | 4-Cl | H | —C₄H₉ | 208° C. Hydrochloride |
| 2-CH₂—C≡CH | H | H | —C₂H₅ | 74° C. |
| 2-CH₃ | 3-CH₃ | 5-CH₃ | —C₃H₇ | 121° C. |

-continued

| R¹ | R² | R³ | R⁴ | W | Melting Point |
|---|---|---|---|---|---|
| 4-OC$_4$H$_9$ | H | H | H | Br | 221° C. Hydrochloride |
| 2-O—CH$_2$—OH≡CH$_2$ | H | H | H | Br | 166° C. - HCl |
| 4-NH—CO—N⟨O⟩ | H | H | H | Br | 208° C. - HCl |
| 2-O—CH$_2$—C≡CH | H | H | H | Br | 188° C. - HCl |
| 2-CH$_3$ | 4-CH$_3$ | H | CH$_3$ | Br | 87° C. |
| 2Cl | H | H | H | Br | 159° C. |
| 3-OCH$_3$ | H | H | H | Br | 162° C. |
| 2-OC$_2$H$_5$ | H | H | H | Br | 200° C. - HCl |
| 2-Cl | H | H | H | H | 143° C. |
| 3-CH$_3$O | H | H | H | H | 149° C. |
| 2-OC$_2$H$_5$ | 4-Cl | H | H | H | 168° C. |
| 2-O—CH$_2$—CH=CH$_2$ | 4-OCH$_3$ | H | H | H | 154° C. |

The substantial technical superiority of the compounds of the instant invention over a typical representative of known commercial products identical in action and similar in chemical structure, namely metoprolol, is obvious from the following comparative pharmacological data.

I. Structures of the Compounds Compared

1. Compound of the Invention

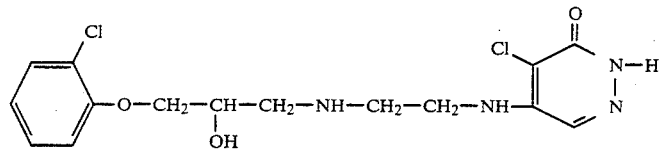

2. Metoprolol

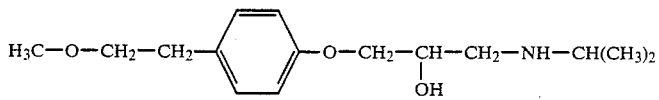

II. Action on the Circulation of anesthesized Dogs

1. β-Receptor Blockage

In dogs undr pentobarbital anesthesia the compound of the invention impedes the rise in contractility and heart rate induced by isoprenalin with an ED of 0.003 mg/kg intravenously, whereas in the case of metoprolol the corresponding value is 0.14 mg/kg. The action of the compound of the invention thus exceeds that of metoprolol by a factor of 40 (and that of propanolol by a factor of 11).

Comparing the blockage of the cardiac β-receptors with that of the blood vessels gives a cardioselectivity ratio ED$_{50}$ (heart): ED$_{50}$ (vessel) of 1:76 for the compound of the invention and 1:18 for metoprolol. The compound of the invention thus features a pronouncedly greater cardioselectivity.

2. Hemodynamics

The hemodynamic profile of action of the compound of the invention in dogs under pentobarbital anesthesia is characterised by a marked drop in the left ventricular end-diastolic (LVEDP-2 mm Hg, metoprolol+2 mm Hg) blood pressure (−35 mm Hg at 0.05 mg/kg intravenously, metoprolol −5 mm HG) and in the total peripheral resistance (TPR-1191 dyn sec cm$^{-5}$, metoprolol-135 dyn sec cm$^{-5}$) without being accompanied by a lowering of the cardic contractility which is pronounced in metoprolol especially in higher doses.

In the case of the compound of the invention a lowering of the cardiac contractility and performance is prevented by a moderate intrinsic sympathomimetic activity (ISA) corresponding to approx. ⅓ of that of pindolol.

The compound of the invention thus displays a more favourable hemodynamic profile of action than metoprolol as it reduces the cardiac after-load via a lowering of the TPR on the one hand and the preload on the other without producing a negative inotropic action.

III. Action on awake renal-hypertonic Dogs compounds of the invention and a compound of the formula

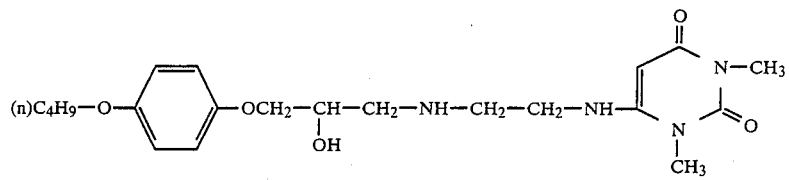

At a dosage of 3.0 mg/kg metoprolol, administered perorally, has practically no acute hypotensive action which is known from German Offenlegungsschrift No. 2,819,629 and comparable in structure:

| $R^1$ | $R^2$ | $R^3$ | $R^4$ | X | $\beta_1$-Blockade $ED_{50}$ mg/kg | | Cardioselectivity $\frac{ED_{50} \text{ heart}}{ED_{50} \text{ vessel}}$ | LVEDP Dosis mg/kp/$\Delta$p [mbar] | | TPR Dosis/ $\left[\frac{\text{dyn cm}}{\text{sec}^5}\right]$ | |
|---|---|---|---|---|---|---|---|---|---|---|---|
| 2-Cl | H | H | H | Cl | 0.05 0.003 | i.d. i.d. | $\frac{1}{76}$ | 0.05 i.v. | $-2,7$ | 0.05 | $-1191$ |
| 2-OC$_4$H$_9$ | H | H | H | Cl | 0.008 | i.v. | $\frac{1}{30}$ | 0.05 i.v. | $-1,3$ | 0.05 | $-530$ |
| 2-OC$_4$H$_9$ | H | H | —CH$_3$ | Cl | 0.007 | i.v. | $\frac{1}{30}$ | 0.05 i.v. | $-2$ | 0.05 | $-620$ |
| 2-Cl | H | H | H | Br | 0.0008 | i.v. | $\frac{1}{81}$ | | | | |
| | | | | | 0.0023 | i.v. | $\frac{1}{127}$ | | | | |
| 2-OC$_2$H$_5$ | H | H | H | Br | 0.0049 | i.v. | $\frac{1}{20}$ | | | | |
| H | H | H | H | Br | 0.0009 | i.v. | $\frac{1}{743}$ | 0.05 | $-5.33$ | | |
| H | H | H | H | H | 0.009 | i.v. | $\frac{1}{4}$ | | | | |
| Metoprolol | | | | | 0.3 0.14 | i.d. i.v. | $\frac{1}{18}$ | | $+2.7$ | 0.05 | $-135$ |
| Compound known from DE-OS 28 19 629 | | | | | 0.0096 | i.v. | | 4.0 i.v. | 0 | 0.05 | 0 |

| $R^1$ | $R^2$ | $R^3$ | $R^4$ | X | Blood Pressure Dosis mg/kg/$\Delta P_s$/$\Delta P_d$[mbar] | | | ISA | Strophanthin-k Blockage of Arrhytmias |
|---|---|---|---|---|---|---|---|---|---|
| 2-Cl | H | H | H | Cl | 0.2 | p.o. | $-37$ $-20$ | $\frac{1}{4}$ | $+$ |
| 2-OC$_4$H$_9$ | H | H | H | Cl | 1 | p.o. | $-53$ $-40$ | | $+$ |
| 2-OC$_4$H$_9$ | H | H | —CH$_3$ | Cl | 0.1 | p.o. | $-33\,3$ $-26.7$ | | $+$ |
| 2-Cl | H | H | H | Br | 0.01 | i.v. | $-20$ $-20$ | | |
| 2-OC$_2$H$_5$ | H | H | H | Br | 0.001 | i.v. | $-40$ $-6.7$ | | |
| H | H | H | H | Br | 0.5 0.025 0.064 | i.v. i.v. i.v. | $-100$ $-66.7$ $-40$ $-33.3$ $-53.3$ $-40$ | | |
| H | H | H | H | H | 0.04 0.01 0.004 | i.v. i.v. i.v. | $-33.3$ $-20$ $-26.7$ $-20$ $-33.3$ $-26.7$ | $\frac{1}{4}$ $\frac{1}{4}$ | — |
| Metoprolol | | | | | 3 0 | | 0 0 | 0 | 0 |
| Compound known from DE-OS 28 19 629 | | | | | 4 0 | i.v. | 0 0 | 0 | 0 |

Abbreviations:
i.v. = intravenous
p.o. = peroral
i.d. = intraduodenal
ED = effective dose on awake renalhypertonic dogs ($\Delta BP_s$ $-6$ mm Hg, $\Delta BP_d$ $-3$ mm Hg) whereas the compound of the invention lowers the systolic blood pressure by $-28$ mm Hg and the diastolic blood pressure by $-15$ mm Hg at a peroral dosage of as low as 0.2 mg/kg.

The pharmacological data of the following tables were obtained by analogous tests with respect to further The values of the intrinsic sympathomimetic activity (ISA) of the above table are indicated relative to pindolol as reference substance.

The pharmaceutical data show that the compounds of the invention display a particularly balanced spectrum of action when contrasted with the closest known compounds.

In addition to the efficiency in the β-blockage which is at least 100% superior to that of the compound known from German Offenlegungsschrift No. 2,819,629, it is the favourable acute hypotensive action and, in particular, the highly balanced intrinsic sympathomimetic activity (ISA) that render the use of the compounds of the invention especially advantageous, the ISA preventing a drop in the contractility without, however, inducing an undesirable rise in the heart rate. A further advantage of the compounds of the invention, in particular over those known from German Offenlegungsschrift No. 2,819,629, is its enhanced histocompatibility. As a result of this, for example, in the case of intravenous administration local stimulation phenomena are prevented to a great extent.

The above-mentioned advantageous combination of actions render the compounds of the invention particularly suitable for the prophylactic and therapeutic treatment of myocardial infarction.

For these purposes, adults are given a daily dose in the range of 5–30 mg. administered either as a single dose or in 2–3 doses.

Peroral or intravenous administration is preferred.

What is claimed is:

1. A physiologically-active and pharmacologically-acceptable basically-substituted pyridazine of formula I

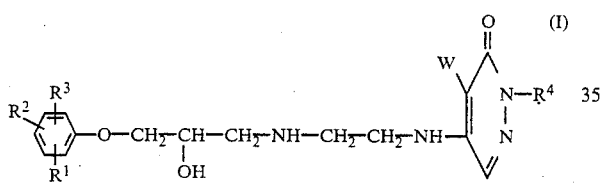

wherein
   each of $R^1$, $R^2$ and $R^3$ is, independently, a member selected from the group consisting of hydrogen; fluorine; chlorine; bromine; hydroxyl; nitro; trifluoromethyl; alkyl having from 1 to 8 C atoms; alkoxyalkyl having from 2 to 6 C atoms; alkenyl having up to 6 C atoms; alkynyl having up to 6 C atoms; cycloalkyl having a ring size of from 5 to 8 C atoms; phenyl; alkoxy having from 1 to 8 C atoms; hydroxyalkoxy having from 2 to 6 C atoms; alkoxyalkoxy having a total of up to 8 C atoms; alkenyloxy having up to 6 C atoms; alkynyloxy having up to 6 C atoms; cycloalkoxy having a ring size of from 5 to 8 C atoms; benzyloxy; phenethoxy; alkanoyl having from 1 to 6 C atoms; acylamino having up to 11 C atoms in the acyl radical; an —NH—CO—$R^9$ radical, $R^9$ being a member selected from the group consisting of morpholino, piperidino, or 1-pyrrolidinyl; ureido; ureido which is monosubstituted in the 3-position by cycloalkyl having 5 or 6 C atoms; ureido which is monosubstituted or disubstituted in the 3-position by alkyl having 1 to 6 C atoms and/or alkenyl having 3 to 6 C atoms;
   $R^4$ is hydrogen or lower alkyl; and
   W is a member selected from the group consisting of hydrogen, chlorine or bromine; or an acid-addition salt thereof.

2. A physiologically-active and pharmacologically-acceptable basically-substituted pyridazine according to claim 1 of the formula

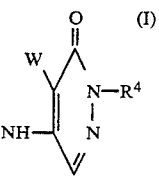

wherein
   $R^1$ is a member selected from the group consisting of hydrogen; fluorine; chlorine; bromine; hydroxyl; nitro; trifluoromethyl; alkyl having from 1 to 8 C atoms; alkoxyalkyl having from 2 to 6 C atoms; alkenyl having up to 6 C atoms; alkynyl having up to 6 C atoms; cycloalkyl having a ring size of from 5 to 8 C atoms; cycloalkenyl having a ring size of from 5 to 8 C atoms; phenyl; alkoxy having from 1 to 8 C atoms; hydroxyalkoxy having from 2 to 6 C atoms; alkoxyalkoxy having a total of up to 8 C atoms; alkenyloxy having up to 6 C atoms; alkynyloxy having up to 6 C atoms; cycloalkoxy having a ring size of from 5 to 8 C atoms; benzyloxy; phenethoxy; alkanoyl having from 1 to 6 C atoms; acylamino having up to 11 C atoms in the acyl radical; an —NH—CO—$R^9$ radical, $R^9$ being selected from the group consisting of morpholino, piperidino or 1-pyrrolidinyl; ureido; ureido which is monosubstituted in the 3-position by cycloalkyl having 5 or 6 C atoms; and ureido which is monosubstituted or disubstituted in the 3-position by alkyl having from 1 to 6 C atoms and/or alkenyl having from 3 to 6 C atoms;
   $R^2$ is a member selected from the group consisting of hydrogen; fluorine; chlorine; bromine; hydroxyl; alkyl having from 1 to 8 C atoms; alkoxyalkyl having from 2 to 6 C atoms; alkenyl having up to 6 C atoms; alkoxy having from 1 to 8 C atoms; hydroxyalkoxy having from 2 to 6 C atoms; and alkoxyalkoxy having a total of up to 8 C atoms;
   $R^3$ is a member selected from the group consisting of hydrogen; alkyl having 1 to 8 C atoms; and alkoxy having from 1 to 8 C atoms;
   $R^4$ denotes hydrogen or lower alkyl, and
   W is a member selected from the group consisting of hydrogen, chlorine or bromine;
or an acid-addition salt thereof.

3. A physiologically-active and pharmacologically-acceptable compound according to one of claims 2 and 1, characterised in that one of the substituents $R^1$, $R^2$ or $R^3$ denotes alkoxyalkoxy having a total of up to 8 C atoms and the other two denote hydrogen.

4. A physiologically-active and pharmacologically-aceptable compound according to one of claims 2 and 1, characterised in that one of the substituents $R^1$, $R^2$ or $R^3$ denotes alkoxyalkyl having 2–6 C atoms and the other two denote hydrogen.

5. A physiologically-active and pharmacologically-acceptable compound according to one of claims 2 and 1, characterised in that one of the substituents $R^1$, $R^2$ or $R^3$ denotes hydroxyalkoxy having 2 to 6 C atoms and the other two denote hydrogen.

6. A physiologically-active and pharmacologically-acceptable compound according to one of claims 2 and 1, characterised in that one of the substituents $R^1$, $R^2$ or $R^3$ denotes alkoxy having 1 to 8 C atoms and the other two denote hydrogen.

7. A physiologically-active and pharmacologically-acceptable compound according to one of claims 2 and 1, characterised in that one of the substituents $R^1$, $R^2$ or $R^3$ denotes hydroxyl and the other two denote hydrogen.

8. A physiologically-active and pharmacologically-acceptable compound according to one of claims 2 and 1, characterised in that one of the substituents $R^1$, $R^2$ or $R^3$ denotes halogen and the other two denote hydrogen.

9. The compound according to claim 1 of the formula

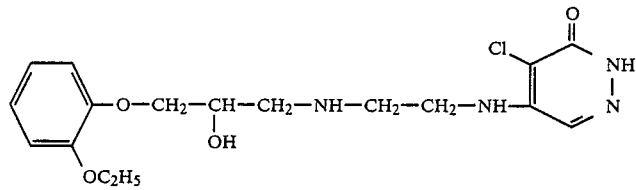

or a pharmaceutically-acceptable acid-addition salt.

10. The compound according to claim 1 of the formula

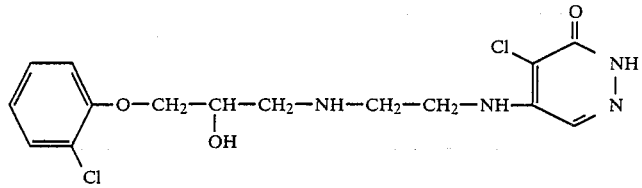

or a pharmaceutically-acceptable acid-addition salt.

11. The compound according to claim 1 of the formula

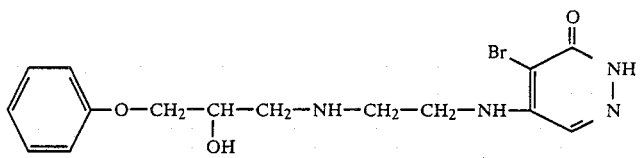

or a pharmaceutically-acceptable acid-addition salt.

12. The compound according to claim 1 of the formula

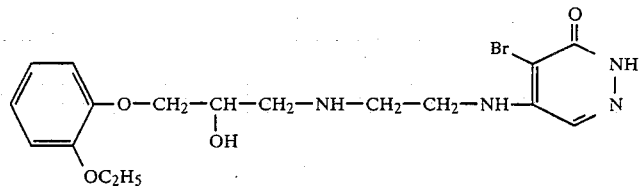

or a pharmaceutically-acceptable acid-addition salt thereof.

13. The compound according to claim 1 of the formula

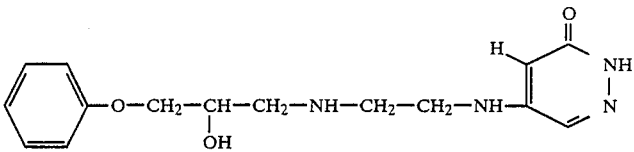

or a pharmaceutically-acceptable acid-addition salt thereof.

14. The compound according to claim 1 of the formula

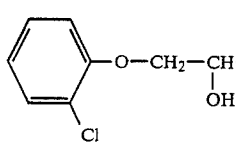 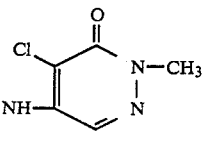

or a pharmaceutically-acceptable acid-addition salt.

15. A pharmacologically-acceptable acid-addition salt of a compound according to claim 1.

16. A substantially non-toxic pharmaceutical preparation containing an effective dose of a basically-substituted pyridazine of formula I, or an acid-addition salt thereof, according to one of claims 2 and 1, in addition to pharmaceutically-permissible excipient and/or additive.

17. A substantially non-toxic pharmaceutical preparation according to claim 16, additionally containing one, or several, other pharmaceutically-active substances.

18. A physiologically-active and pharmacologically-acceptable compound according to claim 1, characterized in that only one of the substituents $R^1$, $R^2$ or $R^3$ is not hydrogen.

19. A physiologically-active and pharmacologically-acceptable compound according to claim 1, characterized in that $R^4$ is hydrogen.

20. A physiologically-active and pharmacologically-acceptable compound according to claim 18, characterized in that $R^4$ is hydrogen.

* * * * *